United States Patent [19]

Otsuka et al.

[11] Patent Number: 5,696,331

[45] Date of Patent: Dec. 9, 1997

[54] APPARATUS FOR DETECTING METAL POWDER AMOUNT IN HYDRAULIC CIRCUIT

[75] Inventors: Kazuo Otsuka; Kunihiko Imanishi; Kenzo Kimoto; Minpei Shoda, all of Hirakata, Japan

[73] Assignee: Kabushiki Kaisha Komatsu Seisakusho, Tokyo, Japan

[21] Appl. No.: 678,121

[22] Filed: Jul. 11, 1996

Related U.S. Application Data

[63] Continuation of Ser. No. 360,721, filed as PCT/JP93/00871, Jun. 25, 1993 published as WO94/00739, Jan. 6, 1994, abandoned.

[30] Foreign Application Priority Data

Jun. 26, 1992 [JP] Japan ................ HEI 4-191410

[51] Int. Cl.⁶ ........................................ G01R 27/02
[52] U.S. Cl. ........................................ 73/865.8
[58] Field of Search ................ 73/865.8; 340/631; 415/118; 417/33, 44.1, 63, 279; 324/204, 698

[56] References Cited

U.S. PATENT DOCUMENTS

| | | | |
|---|---|---|---|
| 3,457,504 | 7/1969 | Arthur et al. | 324/698 |
| 3,686,926 | 8/1972 | Miller et al. | 324/698 |
| 4,030,028 | 6/1977 | Allender | 324/698 |
| 4,100,491 | 7/1978 | Newman, Jr. et al. | 340/631 |
| 4,302,754 | 11/1981 | Magee et al. | 340/631 |
| 4,686,469 | 8/1987 | Lewis | 340/631 |
| 4,823,625 | 4/1989 | Hamilton | 340/631 |
| 4,926,120 | 5/1990 | Veronesi et al. | 324/698 |
| 5,001,424 | 3/1991 | Kellett et al. | 73/53.07 |
| 5,100,805 | 3/1992 | Ziege et al. | |
| 5,457,396 | 10/1995 | Mori et al. | 324/698 |

FOREIGN PATENT DOCUMENTS

| | | |
|---|---|---|
| 3232416 A1 | 3/1984 | Germany. |
| 3810241 A1 | 10/1988 | Germany. |
| 3902339 A1 | 8/1990 | Germany. |
| 61-70208 | 4/1986 | Japan. |
| 63-150440 | 6/1988 | Japan. |
| 3-282246 | 12/1991 | Japan. |
| 4-52331 | 2/1992 | Japan. |

Primary Examiner—Robert Raevis
Attorney, Agent, or Firm—Frishauf, Holtz, Goodman, Langer & Chick

[57] ABSTRACT

An apparatus for detecting an amount of metal powder in a hydraulic circuit for supplying a drain pressurized oil from a hydraulic pump driven by an engine is characterized by comprising a metal powder amount detection sensor (9) disposed in a flow passage of the pressurized oil and adapted to transmit a signal in proportion to an adhering amount of the metal powder and a controller (11) for calculating the metal powder amount from the signal outputted from the metal powder detection sensor and displaying the calculated amount.

8 Claims, 3 Drawing Sheets

APPARATUS FOR DETECTING METAL POWDER AMOUNT IN HYDRAULIC CIRCUIT

This application is a Continuation of application Ser. No. 08/360,721, filed as PCT/JP93/00871, Jun. 25, 1993 published as WO94/00739, Jan. 6, 1994, now abandoned.

FIELD OF THE INVENTION

The present invention relates to an apparatus for detecting a metal powder amount in a hydraulic circuit for supplying a drain pressurized oil from a hydraulic pump of a construction machine to a hydraulic equipment such as a cylinder, motor, etc. thereof.

BACKGROUND TECHNOLOGY

In a hydraulic circuit in which oil in a tank is supplied to a hydraulic equipment such as cylinder, motor, etc. by a hydraulic pump, and a return oil from the hydraulic equipment flows in the tank, equipment is sometimes broken or damaged and hence is not operated. In such case, it is necessary to repair the hydraulic equipment by stopping the operation of the construction machine. However, in general, since the construction machine is operated in an engineering work site at which there is generally no repairing equipment available, it is necessary to move the construction machine to a site at which a repairing equipment is arranged, requiring much time and labor for repairing the construction machine.

For the reason described above, in the prior art, a magnet is disposed in the path of the flow passage of the hydraulic circuit to attract metallic powder generated by the damage or wearing of the hydraulic equipment and to periodically inspect the amount of the metallic powder adhering to the magnet, thereby judging the existence of the damage or degree of the wearing of the hydraulic equipment. However, according to such structure, an operator must judge whether the hydraulic equipment should be repaired or not by his intermittent observation of the amount of the metal powder adhering to the magnet, and accordingly, there often causes a case where the operator fails to properly judge a repairing time for example by overlooking an appropriate repairing time, and in such a case, there arise such a problem as that an oil leaks when the magnet is removed for the periodical inspection.

Accordingly, the present invention aims to provide an apparatus for detecting an amount of metal powder in a hydraulic circuit capable of continuously detecting an amount of metal powder in the hydraulic circuit and exactly judging a repairing time thereof in accordance with the detected amount of the metal powder thereby to prevent a damage of a hydraulic equipment from occurring, and moreover, to prevent an oil from leaking from an oil flow passage because no part is removed for the detection.

DISCLOSURE OF THE INVENTION

In order to achieve the above and other objects, according to the present invention, there is provided an apparatus for detecting an amount of metal powder in a hydraulic circuit for supplying a drain pressurized oil from a hydraulic pump driven by an engine of a construction machine, for example, wherein the apparatus comprises a metal powder amount detection sensor disposed in a flow passage of the pressurized oil and adapted to transmit a signal in proportion to an adhering amount of the metal powder and a controller for calculating the metal powder amount from the signal outputted from the metal powder detection sensor and displaying the calculated amount.

According to this structure, since the amount of the metal powder in the hydraulic circuit can be continuously detected, a time for repairing the hydraulic equipment including the hydraulic circuit can be exactly judged in accordance with the detected metal powder amount, thus preliminarily preventing the hydraulic pump and the hydraulic equipment from being damaged. In addition, since there is no need for disassembling parts of the hydraulic equipment for the detection, the oil can be prevented from leaking from its flow passage.

Further, in the above structure, preferably, the controller transmits an abnormal signal at a time when the calculated metal powder amount is larger than a reference value and is abnormally larger than a preceding measured value. An engine revolution number controller is provided for controlling the engine to be rotated with low speed at a time when the abnormal signal is inputted from the controller and an alarm device is provided for generating an alarm.

According to this structure, when the detected metal powder amount is larger than the reference value and is abnormally larger than the preceding measured value, the engine is controlled to reduce its rotation speed and the alarm device is operated to inform the fact to workers, so that it is possible to prevent the hydraulic equipment from being operated for a long time under the condition invaded by the large amount of the metal powder.

Still preferably, an IC (integrated circuit) memory card is provided for the controller to be capable of being inserted or withdrawn, the IC memory card storing the metal powder amount as data calculated by the controller, in such a manner that when the IC memory card is withdrawn, the controller controls the engine revolution number controller to stop the engine operation and prohibit it from being re-started, and when the data stored in the IC memory card is cleared and is again inserted, the controller controls the engine revolution number controller to allow the engine to start its operation.

According to this structure, since the metal powder amount in an abnormal operation time is stored in the IC memory card, it is possible to set the IC memory card to a personal computer or the like to give repair instruction and the like, and moreover, since the engine is not operated under the invaded state of the large amount of the metal powder in the hydraulic circuit and the hydraulic pump is hence not operated, generation of significant faulty of the hydraulic equipment can be prevented.

BRIEF DESCRIPTION OF THE DRAWINGS

The present invention will become more understandable from the following detailed explanation and accompanying drawings showing an embodiment of the present invention. Further, the embodiment represented by the accompanying drawings is provided for easy understanding of the explanation of the invention.

In the accompanying drawings.

DETAILED DESCRIPTION

Hereunder, a metal powder amount detecting apparatus for a hydraulic circuit according to a preferred embodiment of the present invention will be described with reference to FIGS. 1 through 6.

Figure 1:
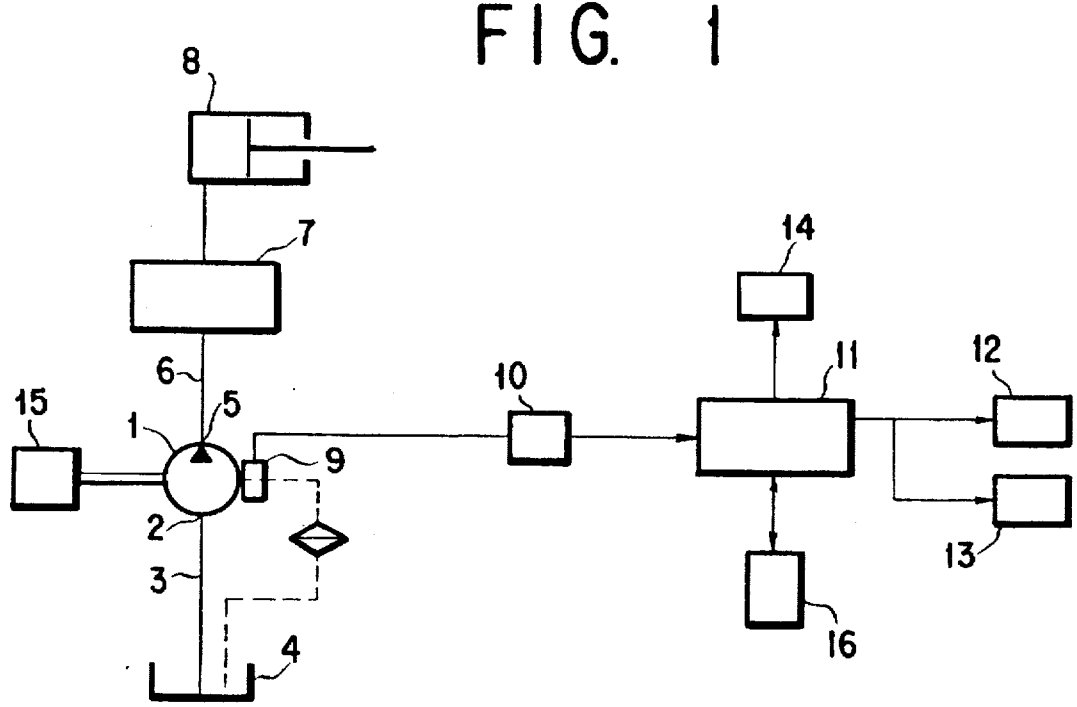
FIG. 1 is a diagram showing a hydraulic circuit provided with one embodiment of a metal powder amount detecting apparatus according to the present invention.

In a hydraulic circuit shown in FIG. 1, a suction port 2 of a hydraulic pump 1 driven by an engine 15 is communicated with an interior of a tank 4 through a suction tube 3 and a drain port 5 thereof is connected to an inlet side of an operation valve 7 through a line 6. An outlet side of the operation valve 7 is connected to a hydraulic equipment 8.

Disposed inside a body of the hydraulic pump 1 is a metal powder amount detection sensor 9, which may be disposed on the side of the hydraulic equipment 8, or the suction tube 3, the line 6, a drain port or a discharge port. That is, the metal powder amount detection sensor 9 may be disposed to a certain portion in the flow passage.

The metal powder detection sensor 9 transmits a signal of a magnitude in proportion to the amount of the metal powder adhering to the metal powder amount detection sensor 9, and the thus outputted signal is amplified by an amplifier 10 and then inputted into a controller 11. The controller 11 serves to calculate the amount of the metal powder from the outputted signal, to always display the calculated amount on a display 12, to compare the amount with a preliminarily set reference value, and to output an abnormal signal to an alarm device 13 or an engine revolution number controller 14 at a time when the presently measured value exceeds the reference value. Further, in a case where the measured amount of the metal powder is abnormally larger than the preceding measured value, an abnormal signal is also outputted.

The alarm device 13 generates an alarm to inform an operator at the time when the abnormal signal is inputted. The engine revolution number controller 14 is composed of, for example, an electronic governor controlling the revolution number of the engine 15 for rendering slow the revolution of the engine 15 when the abnormal signal is inputted from the controller 11.

An IC (integrated circuit) memory card 16 is provided for the controller 11 to be capable of being inserted or withdrawn, the IC memory card storing the metal powder amount as data calculated by the controller 11, in such a manner that when the IC memory card is withdrawn, the controller 11 controls the engine revolution number controller 14 to stop the engine operation and prohibit it from being re-started, and when the data stored in the IC memory card is cleared and is again inserted, the controller controls the engine revolution number controller to allow the engine to start its operation.

Figure 2:
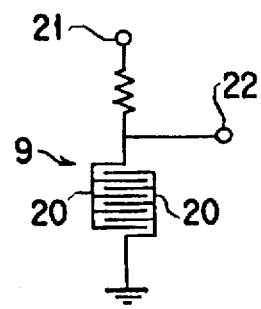
FIG. 2 is a schematic view showing a structure of a metal powder amount detection sensor utilized for the above embodiment.
Figure 3:
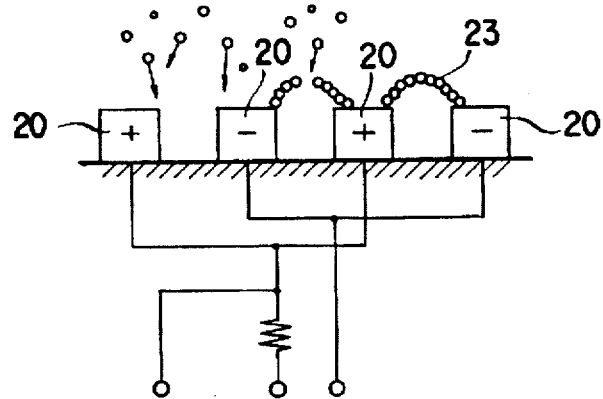
FIG. 3 is an explanatory view for an operation principle of the metal powder amount detection sensor.

The metal powder detection sensor 9 comprises, as shown in FIG. 2, a pair of comb-shaped electrodes 20, 20 facing the flow passage and terminals 21 and 22 connecting a power source, not shown, and the controller 11 to one of the comb-shaped electrodes 20. Then, as shown in FIG. 3, when the metal powder particles 23 adhere between the paired comb-shaped electrodes 20 and 21 to form a bridge therebetween, a current representing a pulse number (frequency) and a pulse voltage which are respectively in proportion to the particle number and the particle diameter of the metal powder 23, flows between the paired comb-shaped electrodes 20 and 20, and the current is inputted an output signal into the controller 11. In the controller 11, the amount of the metal powder is calculated in response to these pulse number and pulse voltage values. The details of such principle are disclosed in Japanese Patent Laid-open Publication No. HEI 3-282246.

Figure 4:
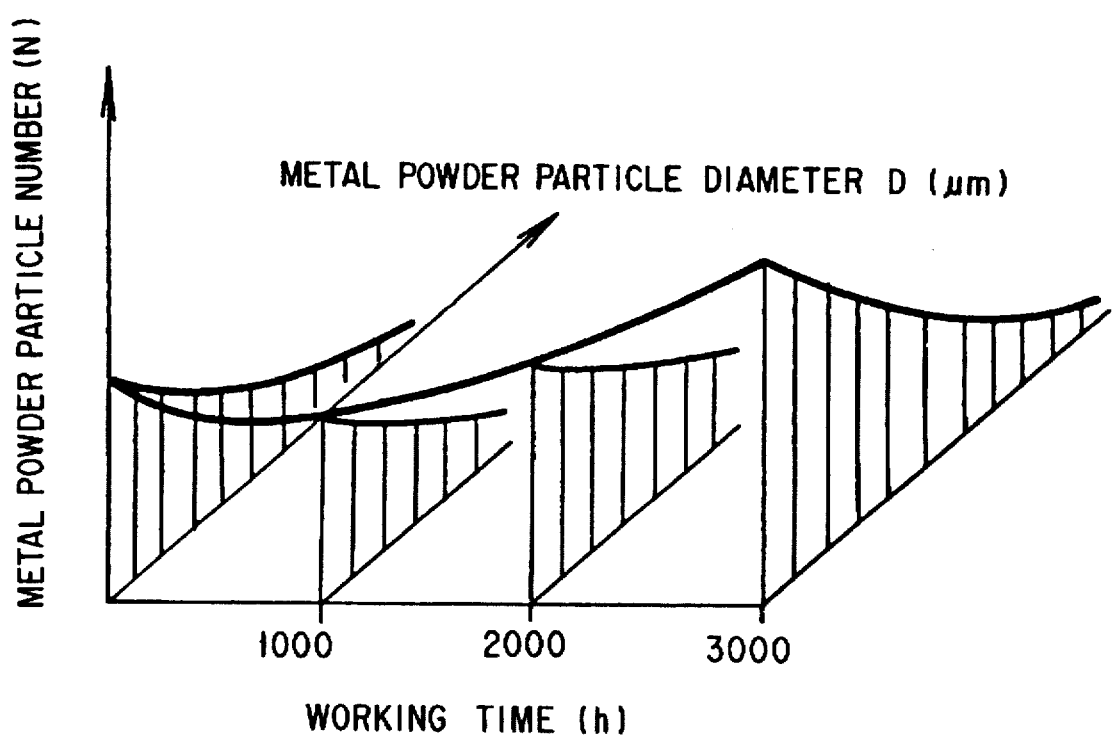
FIG. 4 is a graph showing a reference value of the number of metal powder particles per respective metal powder particle diameters with respect to a working time.

In the controller 11, as shown in FIG. 4, the reference value of the normal metal powder particles per respective diameters of the metal powder particles with respect to the working time in a normal hydraulic circuit is preliminarily set. For example, the number of the metal powder particles per respective diameters thereof is measured by the actual hydraulic circuit in predetermined time intervals to thereby obtain the reference value thereof and such reference value is set in the controller 11. Herein, the amount of the metal powder is sum of the amount obtained by the following expression.

Metal Powder Amount=Metal Powder Particle Diameter×Number of Metal Powder Particles Further, in the controller 11, a measurement difference assumed as an abnormal increasing between the continuously measured two values is preliminarily set to a predetermined value. This value is derived from an actually measured value at a time when a faulty condition is created by utilizing the actual hydraulic circuit.

The operation of the present embodiment will be described hereunder.

Figure 5:
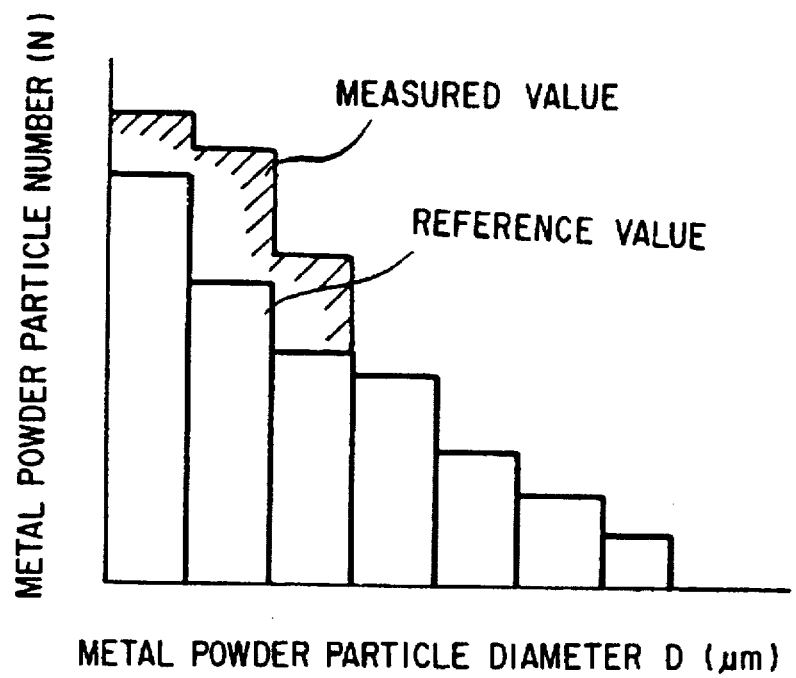
FIG. 5 is a graph showing a case where a measured value of the metal powder amount exceeds the reference value.

The numbers of the metal powder particles and the diameters thereof in the oil following the flow passage in the hydraulic circuit are continuously measured by the metal powder amount detection sensor 9 during the operation of the hydraulic equipment, and the pulse numbers and the output pulse signals of the pulse voltage corresponding to the measured metal powder particle numbers and the metal powder particle diameters are inputted into the controller 11 together with the working time of the hydraulic equipment. In the controller 11, the metal powder amount is calculated by the output pulse signals and is then displayed on the display device 12 and stored in the IC memory card as data. At the same time, the metal powder amount is compared with the preliminarily set reference value with respect to the working time, and as shown in FIG. 5, an abnormal signal is outputted at a time when the measured value exceeds the reference value on the judgement of an occurrence of an abnormal condition. That is, since the metal powder amount increases together with the working time, the measured metal powder amount and the reference metal powder amount with respect to the working time are compared and, in accordance with this comparison, an abnormal signal is outputted.

On the occurrence of such abnormal signal, the alarm device 13 operates thereby to generate an alarm, and then, the revolution numbers (rpm) of the engine 15 is lowered by the engine revolution number controller 14 and this abnormal condition is displayed on the display device 12. In accordance with this displayed fact, an operator confirms the fact that the hydraulic pump or the hydraulic equipment is abnormally worn or damaged, and then, he takes a necessary procedure, so that a fault of the hydraulic equipment can be prevented and repaired.

Figure 6:
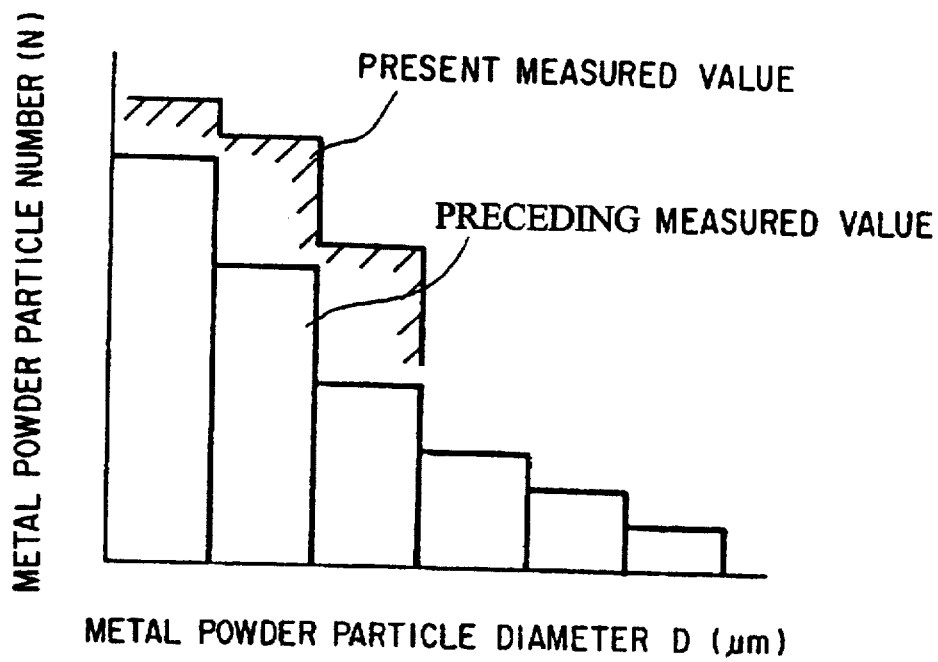
FIG. 6 is a graph showing a case where a presently measured value of the metal powder amount in a certain measuring time abnormally exceeds that of the preceding measuring time.

Furthermore, as shown in FIG. 6, the controller 11 compares the immediately preceding measured value with the measured value of this time, and in a case where the presently measured value abnormally exceeds the preceding measured value, the controller 11 generates an abnormal signal. Then, as described above, the alarm device 13 is operated, the engine revolution number controller 14 operates to lower the revolution number of the engine 15 and such abnormal condition is displayed on the display device 12. Accordingly, the operator detects the fact that the metal powder amount rapidly increases and, then, he takes a necessary procedure, so that an unexpected fault of the hydraulic equipment can be prevented from resulting in a major fault of an entire system including the hydraulic equipment.

As one of the necessary procedures, insertion or withdrawal of the IC memory card will be provided.

That is, the IC memory card 16 is always inserted into the controller 11 to store the metal powder amount as data, and when the controller 11 generates an abnormal signal, the IC memory card 16 reads the abnormal value data at that time and is stored. When this IC memory card 16 is withdrawn from the controller 11, the controller 11 operates to stop the engine 15 and then to prohibit the re-starting the engine 15 through the engine revolution number controller 14.

In the next process, when the IC memory card 16 is set to a personal computer, the personal computer reads out the abnormal data from the IC memory card 16, judges the abnormality and degradation (remaining life time) in accordance with the preliminarily set data and instructs the inspection and repairing of the hydraulic circuit in accordance with the preliminarily set program.

Finally, when the data stored in the IC memory card 16 is cleared and the IC memory card 16 is inserted into the controller 11, the controller 11 enables the engine 15 to start through the engine revolution number controller 14.

Further, the present invention is described with reference to the exemplary embodiment, but it should be apparent to those skilled in the art that various changes, eliminations and additions may be made with respect to the disclosed embodiment without departing from the subject and scope of the present invention. Accordingly, it is to be understood that the present invention is not limited to the above-described embodiment and includes equivalents of the elements recited in the appended claims.

Possibility of Industrial Usage

As described hereinbefore, the metal powder amount detecting apparatus of a hydraulic circuit according to the present invention is extremely useful for the prevention of fault and accident of a hydraulic equipment in a construction machine or the like.

We claim:

1. An apparatus for detecting an amount of metal powder in a hydraulic circuit for supplying a drain pressurized oil from a hydraulic pump driven by an engine, said metal powder amount detecting apparatus comprising:

a metal powder amount detection sensor disposed directly in a flow passage of the pressurized oil so as to directly contact the pressurized oil, and arranged to continuously output a signal which is a function of an amount of metal powder adhering thereto;

a controller which continuously calculates, on a real time basis, metal powder amounts based on the signal continuously output by said metal powder amount detection sensor;

a memory which stores the metal powder amounts continuously calculated by said controller; and a display unit which displays the metal powder amounts continuously calculated by said controller;

wherein said controller includes means for comparing a calculated metal powder amount with a stored reference value, on a real time basis, and outputting an abnormal signal at a time when the calculated metal powder amount is abnormally larger than the reference value; and an engine revolution control unit which controls operation of the engine, said engine revolution control unit controlling the engine to be rotated at a low speed when said abnormal signal is output by said controller;

wherein:

said memory comprises an IC (integrated circuit) memory card which stores the metal powder amounts calculated by said controller, said IC memory card being removably inserted into said metal powder amount detecting apparatus and cumulatively storing the metal powder amounts calculated by said controller; and said controller includes means for controlling said engine revolution control unit to stop and prohibit operation of the engine when said IC memory card is removed from said metal powder detecting apparatus, and means for controlling the engine revolution control unit to enable and start operation of the engine when said IC memory card is inserted into said metal powder amount detecting apparatus.

2. A metal powder amount detecting apparatus according to claim 1, wherein said IC memory card includes means for enabling the metal powder amounts stored therein to be read out and analyzed by a personal computer to determine at least one of an extent of degradation and remaining life of the hydraulic circuit.

3. A metal powder amount detecting apparatus according to claim 1, further comprising an alarm which generates an alarm signal when said abnormal signal is output by said controller.

4. A metal powder amount detecting apparatus according to claim 1, wherein said controller outputs an abnormal signal also at a time when the calculated metal powder amount is abnormally larger than a preceding calculated metal powder amount.

5. An apparatus for detecting an amount of metal powder in a hydraulic circuit for supplying a drain pressurized oil from a hydraulic pump driven by an engine, said metal powder amount detecting apparatus comprising:

a metal powder amount detection sensor disposed in a flow passage of the pressurized oil and arranged to continuously output a signal which is a function of an amount of the metal powder adhering thereto;

a controller which continuously calculates metal powder amounts based on the signal continuously output by said metal powder amount detection sensor;

a memory which stores the metal powder amounts continuously calculated by said controller;

a display unit which displays the metal powder amounts continuously calculated by said controller; and wherein said controller includes means for comparing a calculated metal powder amount with a stored reference value and outputting an abnormal signal at a time when the calculated metal powder amount is abnormally larger than the reference value; and an engine revolution control unit which controls operation of the engine, said engine revolution control unit controlling the engine to be rotated at a low speed when said abnormal signal is output by said controller; and wherein:

said memory comprises an integrated circuit (IC) memory card for storing the metal powder amounts calculated by said controller, said IC memory card being removably inserted into said metal powder amount detecting apparatus and cumulatively storing the metal powder amounts calculated by said controller; and said controller further includes means for controlling said engine revolution control unit to stop and prohibit operation of the engine when said IC memory card is removed from said metal powder amount detecting apparatus, and means for controlling the engine revolution control unit to enable and start operation of the engine when said IC memory card is inserted into said metal powder amount detecting apparatus.

6. A metal powder amount detecting apparatus according to claim 5, wherein said IC memory card includes means for enabling the metal powder amounts stored therein to be read out and analyzed by a personal computer to determine at least one of an extent of degradation and remaining life of the hydraulic circuit.

7. A metal powder amount detecting apparatus according to claim 5, further comprising an alarm which generates an alarm signal when said abnormal signal is output by said controller.

8. A metal powder amount detecting apparatus according to claim 5, wherein said controller outputs an abnormal signal also at a time when the calculated metal powder amount is abnormally larger than a preceding calculated metal powder amount.

* * * * *